United States Patent
Kanesaka

(10) Patent No.: US 11,298,516 B2
(45) Date of Patent: Apr. 12, 2022

(54) APPLICATION CONTAINER AND APPLICATION TOOL

(71) Applicant: KOBAYASHI PHARMACEUTICAL CO., LTD., Osaka (JP)

(72) Inventor: Naoyuki Kanesaka, Ibaraki (JP)

(73) Assignee: KOBAYASHI PHARMACEUTICAL CO., LTD., Osaka (JP)

(*) Notice: Subject to any disclaimer, the term of this patent is extended or adjusted under 35 U.S.C. 154(b) by 518 days.

(21) Appl. No.: 16/084,760

(22) PCT Filed: Mar. 17, 2017

(86) PCT No.: PCT/JP2017/010919
§ 371 (c)(1),
(2) Date: Sep. 13, 2018

(87) PCT Pub. No.: WO2017/169901
PCT Pub. Date: Oct. 5, 2017

(65) Prior Publication Data
US 2019/0076633 A1    Mar. 14, 2019

(30) Foreign Application Priority Data

Mar. 30, 2016 (JP) .............................. JP2016-068755

(51) Int. Cl.
*A61M 35/00* (2006.01)
*B65D 83/00* (2006.01)
(Continued)

(52) U.S. Cl.
CPC ....... *A61M 35/003* (2013.01); *B65D 83/0033* (2013.01); *B05C 17/00503* (2013.01); *B65D 47/42* (2013.01); *B65D 83/38* (2013.01)

(58) Field of Classification Search
CPC .............. A61M 35/003; A61M 35/006; B05C 17/00503; B65D 47/42; B65D 83/0033; B65D 83/38
See application file for complete search history.

(56) References Cited

U.S. PATENT DOCUMENTS 4,533,069 A * 8/1985 Drobish ............. B65D 83/0033
222/209
5,260,062 A * 11/1993 Gaffar ..................... A61K 8/24
424/401
(Continued)

FOREIGN PATENT DOCUMENTS

CN          1210803 A      3/1999
CN       103434736 A     12/2013
(Continued)

OTHER PUBLICATIONS

Machine Translation of JP 2014-221655 obtained from Google Patents (Year: 2014).*
(Continued)

*Primary Examiner* — Benjamin J Klein
(74) *Attorney, Agent, or Firm* — Kratz, Quintos & Hanson, LLP

(57) ABSTRACT

Provided is an application container including a bottom wall, a body section, and a mouth section. The body section includes a base portion, a reduced diameter portion, an interposed portion interposed between the reduced diameter portion and the mouth section, and a back-side neck portion interconnecting the interposed portion and the mouth section at a position opposite to the bottom wall across an axis of the mouth section in a direction orthogonal to the axis. An inner surface of the first belly-side boundary between the base portion and the reduced diameter portion has a shape curved convexly outward. An inner surface of the second belly-side
(Continued)

boundary between the reduced diameter portion and the interposed portion has a shape curved convexly inward.

5 Claims, 6 Drawing Sheets

(51) Int. Cl.
 *B05C 17/005* (2006.01)
 *B65D 47/42* (2006.01)
 *B65D 83/38* (2006.01)

(56) References Cited

U.S. PATENT DOCUMENTS

| | | | | |
|---|---|---|---|---|
| 2005/0063768 | A1* | 3/2005 | Tani | B43K 8/00 |
| | | | | 401/277 |
| 2006/0039742 | A1* | 2/2006 | Cable | A61M 35/003 |
| | | | | 401/134 |
| 2014/0257208 | A1 | 9/2014 | Ueta | |
| 2015/0307237 | A1* | 10/2015 | Kinsman | B65D 35/36 |
| | | | | 401/134 |
| 2016/0214767 | A1* | 7/2016 | Vogel | B65D 51/1611 |
| 2017/0049212 | A1* | 2/2017 | Casasanta, III | A61Q 1/06 |
| 2017/0065800 | A1* | 3/2017 | Weber | A61M 35/003 |
| 2017/0304599 | A1* | 10/2017 | Dombrowski | B65D 1/0238 |
| 2018/0168318 | A1* | 6/2018 | Streeter | A45D 40/261 |
| 2020/0009590 | A1* | 1/2020 | Pinski | B65D 51/2864 |

FOREIGN PATENT DOCUMENTS

| | | |
|---|---|---|
| CN | 204363232 U | 6/2015 |
| GB | 2328926 A | 3/1999 |
| JP | S62-025642 U | 2/1987 |
| JP | H06-042628 U | 6/1994 |
| JP | H09-192236 A | 7/1997 |
| JP | 3076986 U | 4/2001 |
| JP | 2006-232348 A | 9/2006 |
| JP | 2007152138 A | 6/2007 |
| JP | 2012-131561 A | 7/2012 |
| JP | 2014-088206 A | 5/2014 |
| JP | 2014-201332 A | 10/2014 |
| JP | 2014-221655 A | 11/2014 |
| WO | 2013/005434 A1 | 1/2013 |

OTHER PUBLICATIONS

Office Action of corresponding Taiwanese Patent Application No. 106109776 dated Aug. 21, 2020 (11 sheets, 1 sheet translation, 12 sheets total).
International Search Report for International Application No. PCT/JP2017/010919 dated Jun. 13, 2017 (2 Sheets).

* cited by examiner

APPLICATION CONTAINER AND APPLICATION TOOL

TECHNICAL FIELD

The present invention relates to an application tool.

BACKGROUND ART

There has been conventionally known an application tool used for applying a medicinal solution such as a painkiller to skin. For example, Patent Literature 1 (Japanese Patent Application Laid-Open No. 2007-152138) discloses an application tool including an application container that contains a medicinal solution and an application section connected to the application container. The application container includes a bottom wall, a body section having a shape standing from an outer edge of the bottom wall, and a mouth section connected to the body section. The mouth section is opened in a direction crossing a direction normal to the bottom wall. The body section includes a base portion connected to the bottom wall, a reduced diameter portion having a diameter gradually reduced toward the mouth section from the base portion, and a back-side neck portion that interconnects the reduced diameter portion and the mouth section at a position opposite to the bottom wall across the axis of the mouth section in a direction orthogonal to the axis.

Patent Literature 1: Japanese Patent Application Laid-Open No. 2007-152138

By using the application tool as described in Patent Literature 1, it is difficult to apply a medicinal solution to a center part and a region in the vicinity of the center part (hereinafter referred to as the "center part and the like") of the back. When applying a medicinal solution to the center part and the like of the back, the user often applies the medicinal solution by using the application tool over his or her shoulder. Specifically, the user often uses the application tool over his or her shoulder while holding a portion in the vicinity of the bottom wall of the base portion with three fingers, namely, a thumb, an index finger, and a middle finger, in such a downward attitude of the application tool that the application section and the mouth section are positioned lower than the bottom wall. In this case, when the application tool is shifted to the downward attitude from such an upward attitude in which the application section and the mouth section are positioned above the bottom wall, a medicinal solution in the application container is ruffled due to the collision of the medicinal solution against an inner surface of the reduced diameter portion, immediately thereafter further ruffled due to the collision against an inner surface of the back-side neck portion. This generates a large impact force, which may cause the user to drop the application container when he or she holds the portion in the vicinity of the bottom wall of the base portion with the three fingers.

An object of the present invention is to provide an application container and an application tool that are capable of reducing an impact force caused by a medicinal solution when shifted to a downward attitude from an upward attitude.

Provided is an application container capable of containing a medicinal solution, the application container including a bottom wall, a body section that has a shape standing from an outer edge of the bottom wall, and a mouth section connected to an end portion of the body section on a side opposite to the bottom wall, the mouth section being opened in a direction crossing a direction normal to the bottom wall. The body section includes a base portion connected to the bottom wall, a reduced diameter portion having a diameter gradually reduced toward the mouth section from the base portion, an interposed portion interposed between the reduced diameter portion and the mouth section, and a back-side neck portion that interconnects the interposed portion and the mouth section at a position on a side opposite to a side, on which the bottom wall is located, across an axis of the mouth section in a direction orthogonal to the axis. The body section has a first belly-side boundary between the base portion and the reduced diameter portion on the same side as the side on which the mouth section is opened, the first belly-side boundary having an inner surface curved convexly outward. The body section has a second belly-side boundary between the reduced diameter portion and the interposed portion on the same side as the side on which the mouth section is opened, the second belly-side boundary having an inner surface curved convexly inward.

DESCRIPTION OF EMBODIMENTS

Figure 1:
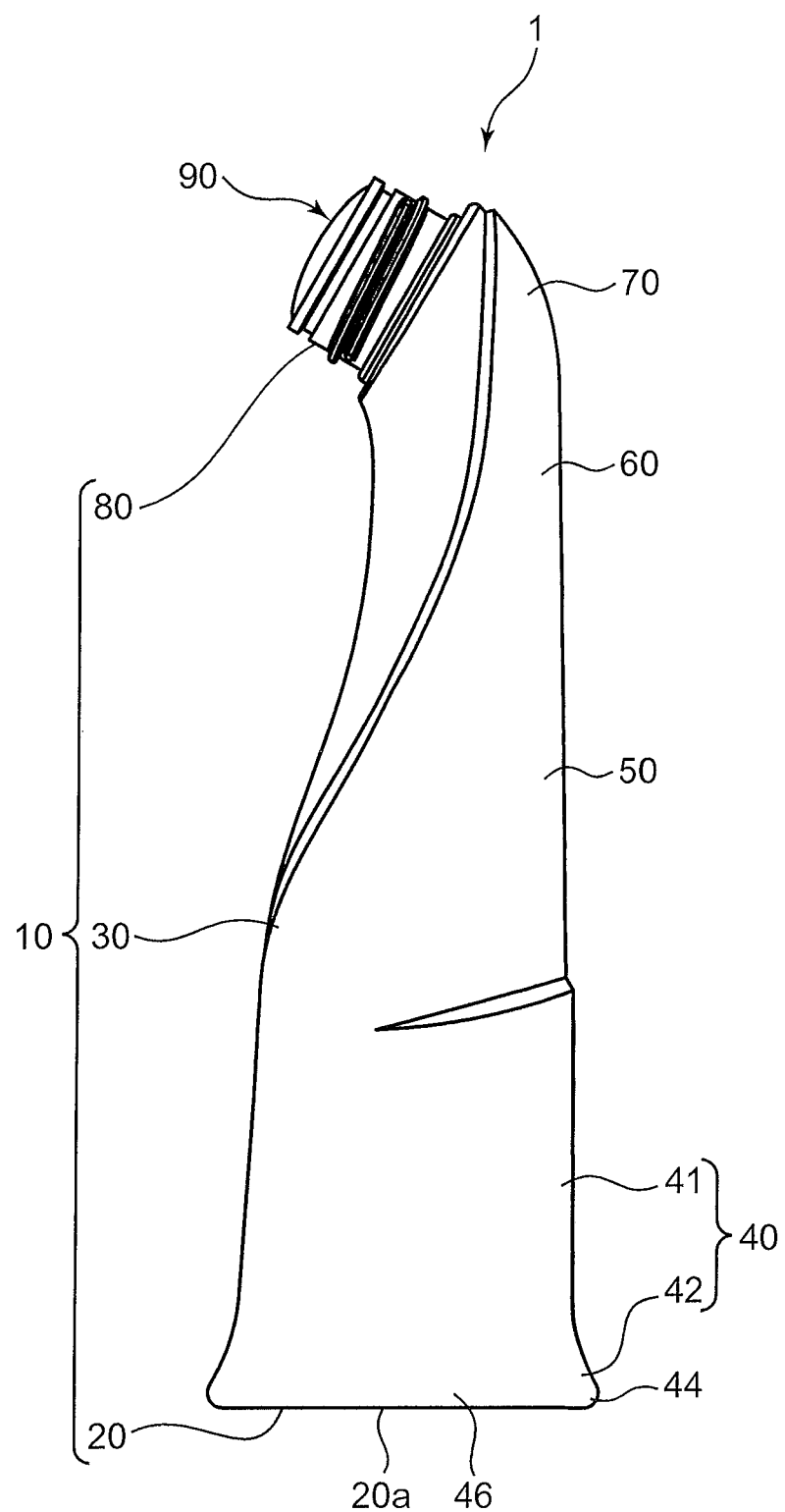
FIG. 1 is a side view of an application tool of an embodiment of the present invention.
Figure 2:
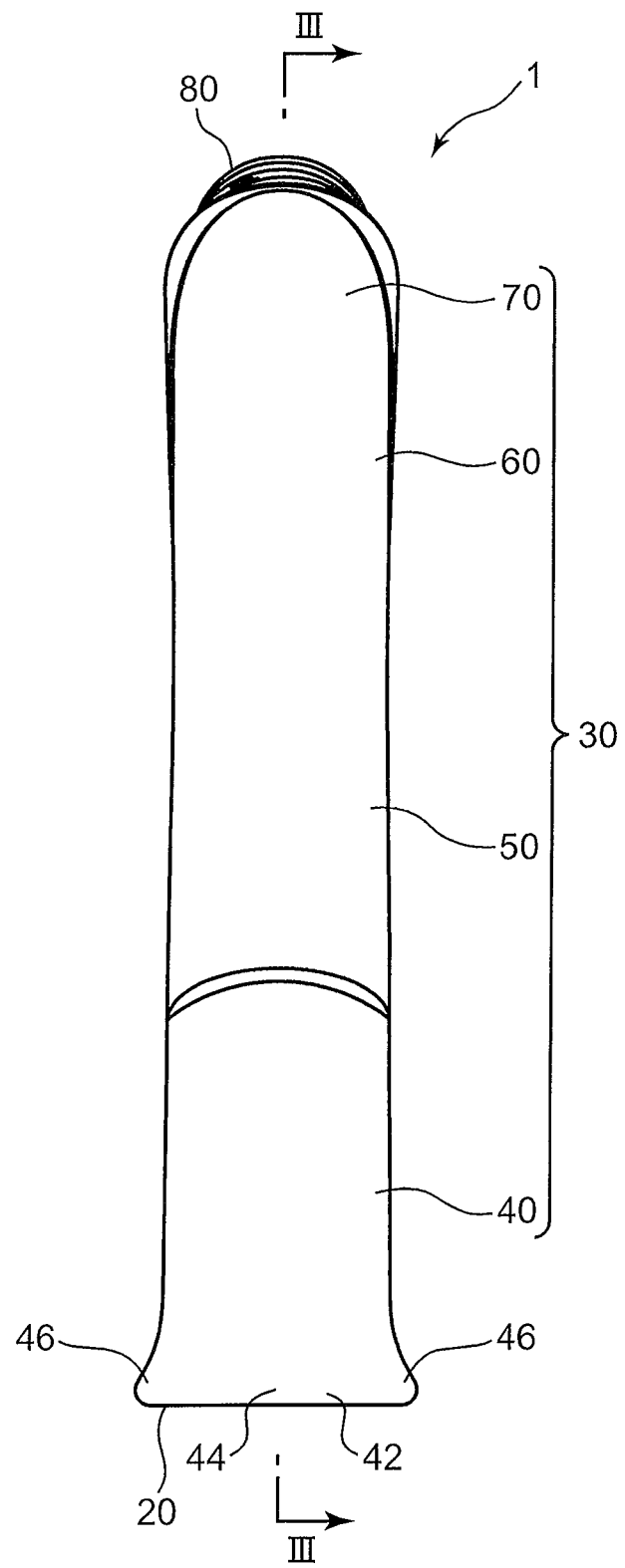
FIG. 2 is a back view of the application tool shown in FIG. 1.
Figure 3:
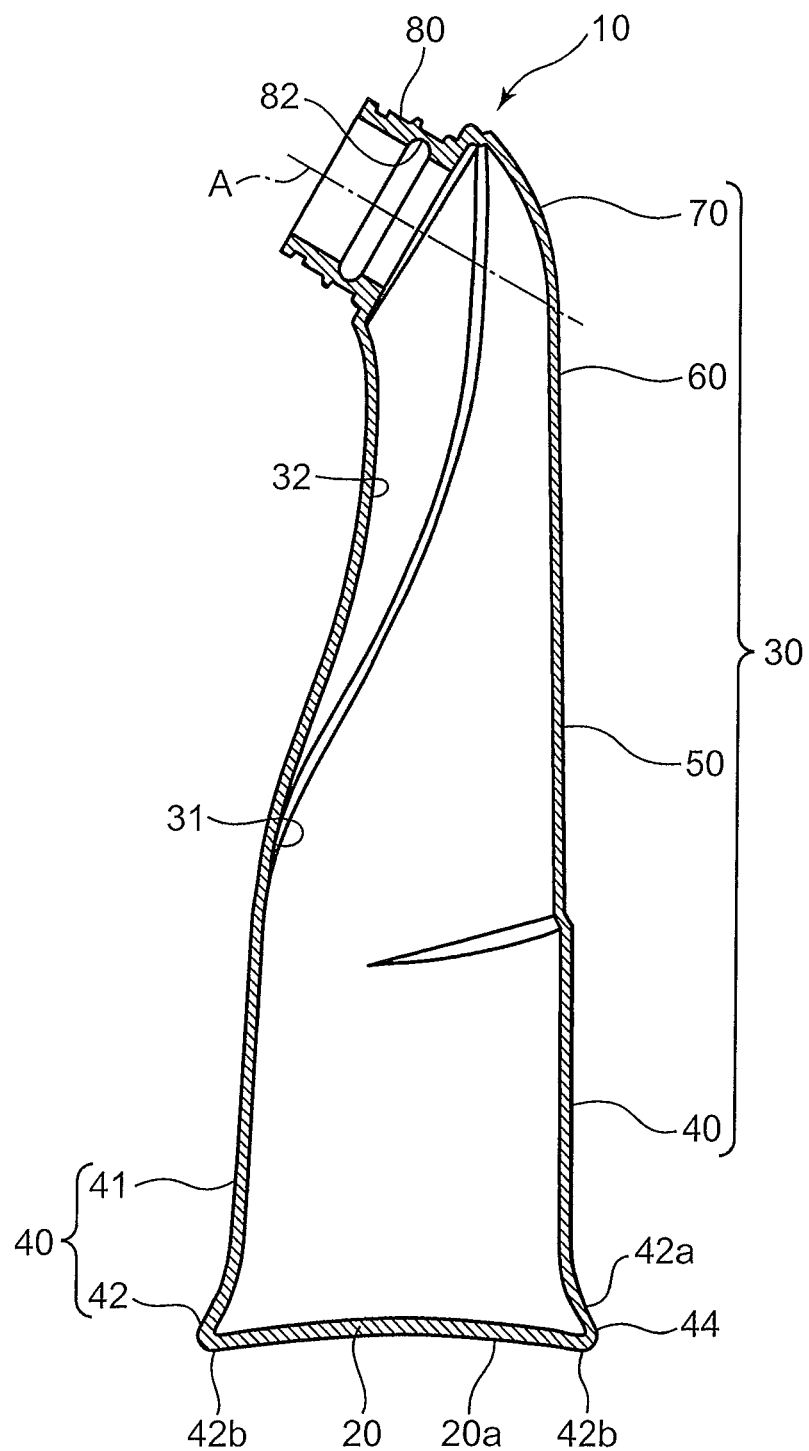
FIG. 3 is a cross-sectional view cut along line of FIG. 2.
Figure 4:
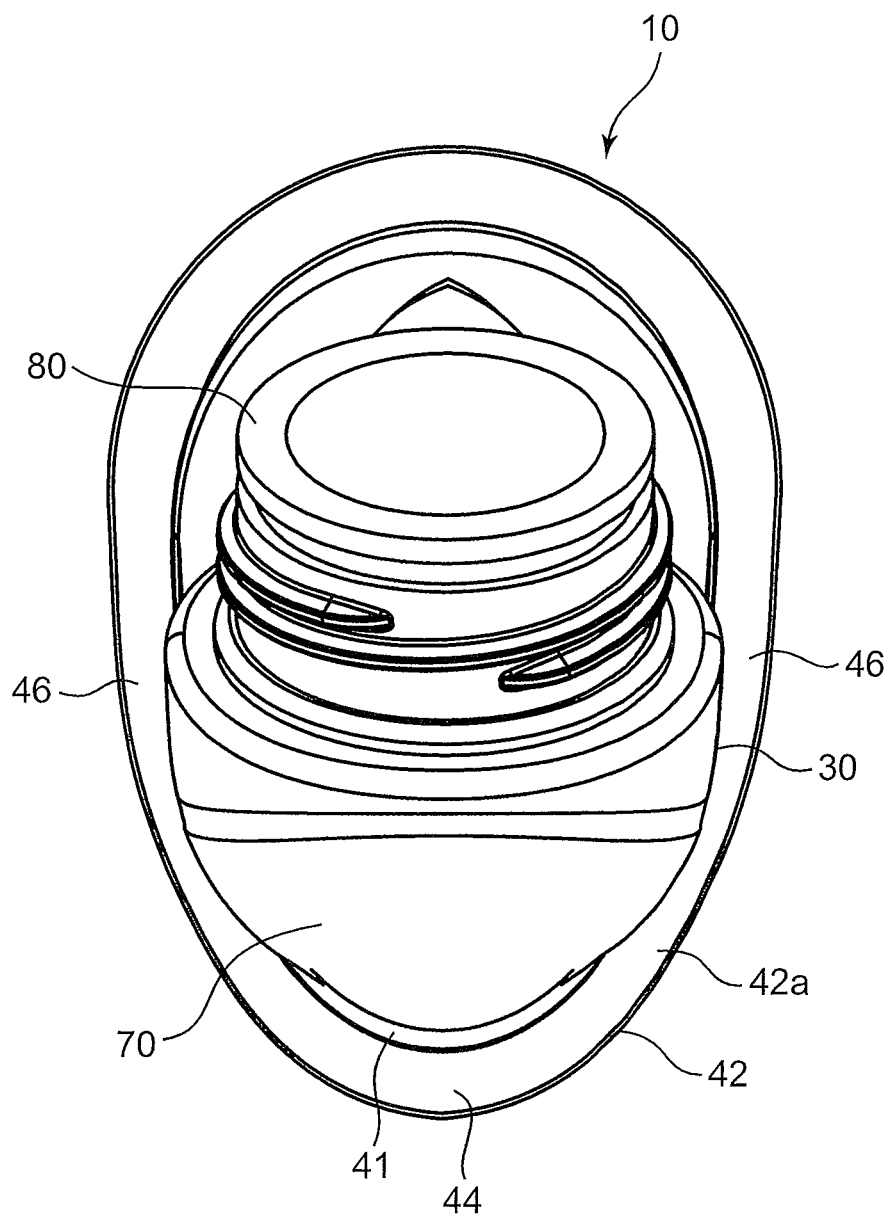
FIG. 4 is a plan view of an application container.

There will be described an application tool 1 according to an embodiment of the present invention with reference to FIGS. 1 to 4. As shown in FIG. 1, the application tool 1 includes an application container 10 and an application section 90. In FIGS. 3 and 4, the application section 90 is not graphically shown.

The application container 10 includes a bottom wall 20, a body section 30, and a mouth section 80.

As shown in FIG. 3, the bottom wall 20 has a shape curved convexly inward (upward in FIG. 3).

The body section 30 has a shape standing up from an outer edge of the bottom wall 20. The body section 30 has a shape extending in a direction normal to the bottom wall 20. The body section 30 includes a base portion 40, a reduced diameter portion 50, an interposed portion 60, and a back-side neck portion 70.

The base portion 40 is connected to the bottom wall 20. The base portion 40 has a substantially cylindrical shape. The base portion 40 will be specifically described later.

The reduced diameter portion 50 has a diameter that is gradually reduced from the base portion 40 toward the mouth section 80.

Specifically, the diameter of the reduced diameter portion 50 is reduced in such a manner that a part of the reduced diameter portion 50 on the same side as a side on which the mouth section 80 is opened (on the left side in FIGS. 1 and 3) becomes closer to a part on the opposite side to the side on which the mouth section 80 is opened (right side in FIGS. 1 and 3) as it approaches the mouth section 80. Hereinafter, the same side as the side on which the mouth section 80 is opened of the body section 30 will be referred to as a belly side and the side opposite to the side on which the mouth section 80 is opened of the body section 30 will be referred to as a back side. There is a first belly-side boundary 31 between the base portion 40 and the reduced diameter portion 50 on the belly side, the first belly-side boundary 31 having an inner surface curved convexly outward.

The interposed portion 60 is interposed between the reduced diameter portion 50 and the mouth section 80. The interposed portion 60 has a part on the belly side, the part being curved convexly inward. The part of the interposed portion 60 on the belly side is connected to the mouth section 80. There is a second belly-side boundary 32 between the reduced diameter portion 50 and the interposed portion 60 on the belly side, the second belly-side boundary 32 having an inner surface curved convexly inward.

The back-side neck portion 70 interconnects the interposed portion 60 and the mouth section 80 at a position on a side opposite to a side on which the bottom wall 20 is positioned, across the axis A of the mouth section 80 in a direction orthogonal to the axis A. In other words, the back-side neck portion 70 interconnects the interposed portion 60 and the mouth section 80 on the back side.

The mouth section 80 is connected to an end portion of the body section 30 on a side opposite to the bottom wall 20 side (on the upper side in FIG. 1). The mouth section 80 is opened in a direction crossing a direction normal to the bottom wall 20. As shown in FIG. 3, the mouth section 80 has an inner circumferential surface formed with a groove portion 82 dented convexly outward radially of the mouth section 80. The groove portion 82 may be omitted. The mouth section 80A can be attached with a cap.

The application section 90 is connectable to the mouth section 80 detachably. The application section 90 is capable of applying a medicinal solution in the application container 10.

The base portion 40 will be described in detail. The base portion 40 includes a base portion main body 41 having a tubular outer circumferential surface and a finger receiving portion 42 allowing the user to put his or her finger on the finger receiving portion 42.

The finger receiving portion 42 is formed in the vicinity of the bottom wall 20 in the base portion main body 41. In the present embodiment, the finger receiving portion 42 has a shape projecting outward beyond the outer circumferential surface of the base portion main body 41 radially of the base portion main body 41. As shown in FIGS. 1 to 3, the finger receiving portion 42 is continuous along a circumferential direction of the base portion main body 41. As shown in FIG. 4, in a plan view, the finger receiving portion 42 has an outline set to be entirely larger than the outline of each of the base portion main body 41, the reduced diameter portion 50, the interposed portion 60, the back-side neck portion 70, the mouth section 80, and the application section 90.

The finger receiving portion 42 includes an upper overhang surface 42a formed on a side closer to the mouth section 80 in a direction joining the bottom wall 20 and the mouth section 80 (vertically in FIG. 1), and a lower overhang surface 42b formed on a side closer to the bottom wall 20 in the direction joining the bottom wall 20 and the mouth section 80.

The upper overhang surface 42a has a shape gradually overhanging outward as it approaches the bottom wall 20. Specifically, the upper overhang surface 42a has a shape curved so as to be convex in a direction from the mouth section 80 toward the bottom wall 20.

The lower overhang surface 42b is smoothly continued with an outer surface 20a of the bottom wall 20. In the present embodiment, as shown in FIG. 3, the lower overhang surface 42b and the outer surface 20a of the bottom wall 20 have a shape curved so as to be entirely convex inward (upward in FIG. 3). The lower overhang surface 42b is contactable to a flat placing surface of a desk or the like simultaneously in the entire area outside the outer edge of the bottom wall 20 radially of the base portion main body 41. There is a boundary between the upper overhang surface 42a and the lower overhang surface 42b, the boundary having a shape curved convexly outward.

Next will be described an example of a method of using the above-described application tool 1. Below will be described a case of applying a medicinal solution to a center part or a part in the vicinity of the center part (hereinafter referred to as the "center part and the like") of the back with the application tool 1 over a shoulder.

The user holds a portion in the vicinity of the bottom wall 20 of the base portion 40, that is, the finger receiving portion 42, with three fingers, namely, a thumb, an index finger, and a middle finger. Specifically, the user lays the index finger on a part of the finger receiving portion 42 on the side (the right side in FIG. 1) opposite to the side on which the mouth section 80 is opened (hereinafter the part is referred to as the "back-surface finger receiving portion 44"), and also lays the thumb and the middle finger on respective parts on opposite sides in a direction (lateral direction in FIGS. 2 and 4) orthogonal to a direction that joins the side on which the mouth section 80 is opened and the opposite side of the finger receiving portion 42 (hereinafter the respective parts are referred to as the "pair of side-surface finger receiving portions 46").

In this state, the attitude of the application tool 1 is changed from an upward attitude in which the application section 90 and the mouth section 80 are positioned above the bottom wall 20 to a downward attitude in which the application section 90 and the mouth section 80 are positioned below the bottom wall 20. The medicinal solution in the application container 10 is thereby flowed toward the mouth section 80.

In the present application container 10, since the inner surface of the first belly-side boundary 31 is curved to be convex outward and the inner surface of the second belly-side boundary 32 is curved to be convex inward, the medicinal solution is restrained from ruffling at the boundaries 31 and 32 when the application tool 1 is shifted to the downward attitude from the upward attitude. Furthermore, the interposed portion 60, interposed between the reduced diameter portion 50 and the mouth section 80, enables a long distance to be secured from the second belly-side boundary 32 to the back-side neck portion 70, allows the medicinal solution having passed through the second belly-side boundary 32 when the application tool 1 is shifted from the upward attitude to the downward attitude to be straightened in the interposed portion 60. This reduces an impact force generated by the collision of the medicinal solution against the inner surface of the back-side neck portion 70. The application tool 1 is thus restrained from being dropped from the user when being shifted to the downward attitude from the upward attitude while the finger receiving portion 42 is held with the three fingers, namely, the thumb, the index finger, and the middle finger.

In addition, the back surface finger receiving portion 44 capable of receiving the index finger thereon and the pair of the side-surface finger receiving portions 46 capable of receiving the index finger and the middle finger thereon enable the application container 10 to be more reliably restrained from being dropped from the user when the application container 10 is shifted to the downward attitude from the upward attitude.

Besides, the groove portion 82 formed in the inner circumferential surface of the mouth section 80 can further suppress the ruffling of the medicinal solution in the groove portion 82. The disturbance of a medicinal solution flowing out of the mouth section 80 is also suppressed.

When the application container 10 is placed on a flat placing surface of a desk or the like, the entire back-surface lower overhang surface of the back-surface finger receiving portion 44 on the side closer to the bottom wall 20 in a direction joining the bottom wall 20 and the mouth section 80 and the entire lower overhang surface 42b of the pair of the side finger receiving portions 46 including the side-surface lower overhang surface on the side closer to the bottom wall 20 in the direction joining the bottom wall 20 and the mouth section 80 are brought into contact with the placing surface simultaneously outside outer edge of the bottom wall 20; this allows the application container 10 from falling down when placed on the placing surface as compared to the case where only the outer surface 20a of the bottom wall 20 can make contact with the placing surface.

The above embodiment disclosed in the description is an exemplification in every aspect, and not to be considered as restrictive. The scope of the present invention is shown by claims and not by the description described above, and includes all changes made within the meaning and the scope equal to those of claims.

Figure 5:
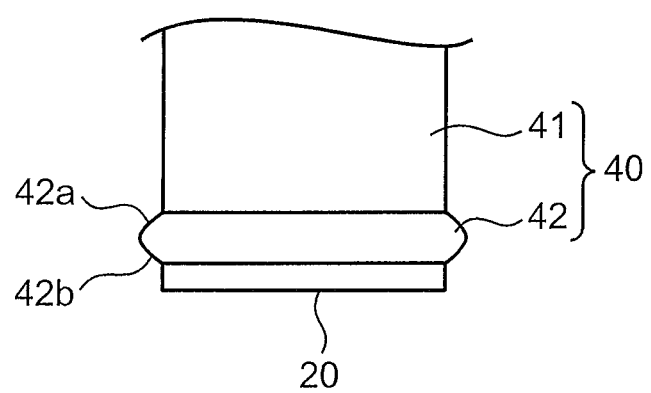
FIG. 5 is a diagram showing a variation of a back-surface finger receiving portion and a pair of finger receiving portions.

For example, as shown in FIG. 5, the lower overhang surface 42b of the finger receiving portion 42 may be separated from the outer surface 20a of the bottom wall 20 toward the mouth section 80 side. In short, the lower overhang surface 42b and the outer surface 20a of the bottom wall 20 do not have to form a flush surface.

Figure 6:
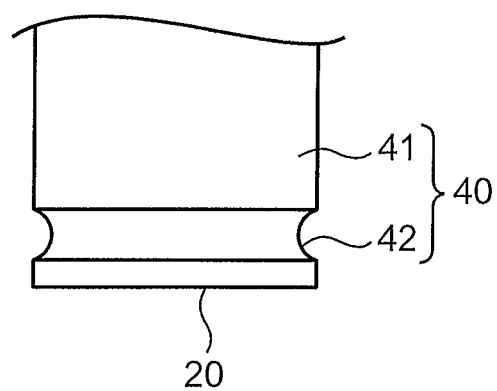
FIG. 6 is a diagram showing a variation of the back-surface finger receiving portion and the pair of the finger receiving portions.

Alternatively, as shown in FIG. 6, the finger receiving portion 42 may have a shape dented to be convex inward radially of the base portion main body 41 beyond the outer circumferential surface of the base portion main body 41.

A part of the finger receiving portion 42 may be omitted except for the back-surface finger receiving portion 44 and the pair of the side-surface finger receiving portions 46.

A plurality of the groove portions 82 may be provided to the inner circumferential surface of the mouth section 80.

The outer surface 20a of the bottom wall 20 and the lower overhang surface 42b may be formed to be flat.

As described above, provided is an application container capable of containing a medicinal solution, the application container including a bottom wall, a body section that has a shape standing from an outer edge of the bottom wall, and a mouth section connected to an end portion of the body section on a side opposite to the bottom wall, the mouth section being opened in a direction crossing a direction normal to the bottom wall. The body section includes a base portion connected to the bottom wall, a reduced diameter portion having a diameter gradually reduced toward the mouth section from the base portion, an interposed portion interposed between the reduced diameter portion and the mouth section, and a back-side neck portion that interconnects the interposed portion and the mouth section at a position on a side opposite to a side, on which the bottom wall is located, across an axis of the mouth section in a direction orthogonal to the axis. The body section has a first belly-side boundary between the base portion and the reduced diameter portion on the same side as the side on which the mouth section is opened, the first belly-side boundary having an inner surface curved convexly outward. The body section has a second belly-side boundary between the reduced diameter portion and the interposed portion on the same side as the side on which the mouth section is opened, the second belly-side boundary having an inner surface curved convexly inward.

In the present application container, the inner surface of the first belly-side boundary being curved convexly outward and the inner surface of the second belly-side boundary being curved convexly inward can restrain a medicinal solution from ruffling at the boundaries when the application container is shifted to a downward attitude (an attitude in which the mouth section is positioned below the bottom wall) from an upward attitude (an attitude in which the mouth section is positioned above the bottom wall). Furthermore, the interposed portion, interposed between the reduced diameter portion and the mouth section to secure a long distance from the second belly-side boundary to the back-side neck portion, allows the medicinal solution having passed through the second belly-side boundary when the application container is shifted to the downward attitude from the upward attitude to be straightened in the interposed portion. This reduces the impact force generated by the collision of the medicinal solution against the inner surface of the back-side neck portion. The application container is thus restrained from being dropped from the user who shifts the application container to the downward attitude from the upward attitude while holding a portion in the vicinity of the bottom wall of the base portion with his or her three fingers, namely, a thumb, an index finger, and a middle finger.

In this case, the mouth section preferably has an inner circumferential surface formed with a groove portion dented convexly outward radially of the mouth section.

This allows the medicinal solution to be further restrained from ruffling in the groove portion, and further allows the disturbance of a medicinal solution flowing out of the mouth section to be suppressed.

In the above application container, the base portion preferably includes a back-surface finger receiving portion formed on a side opposite to a side on which the mouth section is opened, the back-surface finger receiving portion having a shape projecting outward or dented inward, radially of the base portion.

This mode enables an index finger to be received on the back-surface finger receiving portion when a portion in the vicinity of the bottom wall of the base portion is held with three fingers, namely, a thumb, the index finger, and the middle finger, thereby allowing the application container to be more reliably restrained from being dropped from the user when shifted to the downward attitude from the upward attitude.

Specifically, it is preferable that the back-surface finger receiving portion has a shape projecting outward radially of the base portion and the back-surface finger receiving portion has a back-surface lower overhang surface that is contactable to a placing surface at a position outside an outer edge of the bottom wall radially of the base portion.

This involves the contact of the back-surface lower overhang surface with a placing surface of a desk or the like outside the outer edge of the bottom wall when the application container is placed on the placing surface, thereby enabling the application container to be restrained from falling down when the application container is placed on the placing surface as compared with the case where only an outer surface of the bottom wall can make contact with the placing surface.

In the application container, the base portion preferably includes a pair of side-surface finger receiving portions that are formed on opposite sides of the base portion in a direction orthogonal to a direction joining the side on which the mouth section is opened and a side opposite thereto, each of the side-surface finger receiving portions having a shape projecting outward or dented inward radially of the base portion.

This mode allows a thumb and a middle finger to be received on the pair of the side-surface finger receiving portions, respectively, when a portion in the vicinity of the bottom wall of the base portion is held with three fingers, namely, the thumb, an index finger, and the middle finger, which enables the application container to be more reliably restrained from being dropped from the user when the application container is shifted to the downward attitude from the upward attitude.

Specifically, it is preferable that the pair of the side-surface finger receiving portions have respective shapes projecting outward radially of the base portion and the pair of the side-surface finger receiving portions have respective side-surface lower overhang surfaces that are contactable to a placing surface outside an outer edge of the bottom wall radially of the base portion.

This involves the contact of the side-surface lower overhang surface with a placing surface of a desk or the like outside the outer edge of the bottom wall when the application container is placed on the placing surface, thereby enabling the application container to be restrained from falling down when the application container is placed on the placing surface as compared with the case where only an outer surface of the bottom wall can make contact with the placing surface.

The present invention also provides an application tool including the application container and an application section connected to the mouth section of the application container and being capable of applying a medicinal solution in the application container.

The invention claimed is:

1. An application container capable of containing a medicinal solution, the application container comprising:
    a bottom wall;
    a body section that has a shape standing from an outer edge of the bottom wall, the medicinal solution being contained in a space surrounded by the bottom wall and the body section; and
    a mouth section connected to an end portion of the body section on a side opposite to the bottom wall and having an end portion opened in a direction crossing a direction normal to the bottom wall, the end portion of the mouth section being configured to allow an application section to be connected to the end portion of the mouth section, the application section being configured to apply the medicinal solution,
    wherein the body section includes:
    a base portion connected to the bottom wall,
    a reduced diameter portion having a diameter gradually reduced toward the mouth section from the base portion,
    an interposed portion interposed between the reduced diameter portion and the mouth section, and
    a back-side neck portion that interconnects the interposed portion and the mouth section at a position on a side opposite to a side on which the bottom wall is located, across an axis of the mouth section in a direction orthogonal to the axis,
    wherein the body section has a first belly-side boundary between the base portion and the reduced diameter portion on the same side as the side on which the mouth section is opened, the first belly-side boundary having an inner surface curved convexly outward,
    wherein the body section has a second belly-side boundary between the reduced diameter portion and the interposed portion on the same side as the side on which the mouth section is opened, the second belly-side boundary having an inner surface curved convexly inward,
    wherein the mouth section has an inner circumferential surface formed with a curved groove portion between the body section and the application section, the curved groove portion being dented curved convexly outward radially of the mouth section, and coming into contact with the medicinal solution, and
    wherein the groove portion is curved as viewed at a cross-section taken along a direction on which the axis of the mouth section extends.

2. An application container capable of containing a medicinal solution, the application container comprising:
    a bottom wall;
    a body section that has a shape standing from an outer edge of the bottom wall; and
    a mouth section connected to an end portion of the body section on a side opposite to the bottom wall, the mouth section being opened in a direction crossing a direction normal to the bottom wall,
    wherein the body section includes:
    a base portion connected to the bottom wall,
    a reduced diameter portion having a diameter gradually reduced toward the mouth section from the base portion,
    an interposed portion interposed between the reduced diameter portion and the mouth section, and
    a back-side neck portion that interconnects the interposed portion and the mouth section at a position on a side opposite to a side on which the bottom wall is located, across an axis of the mouth section in a direction orthogonal to the axis,
    wherein the body section has a first belly-side boundary between the base portion and the reduced diameter portion on the same side as the side on which the mouth section is opened, the first belly-side boundary having an inner surface curved convexly outward,
    wherein the body section has a second belly-side boundary between the reduced diameter portion and the interposed portion on the same side as the side on which the mouth section is opened, the second belly-side boundary having an inner surface curved convexly inward,
    wherein the base portion includes a back-surface finger receiving portion formed on a side opposite to a side on which the mouth section is opened,
    wherein the back-surface finger receiving portion has a shape projecting outward radially of the base portion and is adjacent to the bottom wall,
    wherein the back-surface finger receiving portion has a back-surface lower overhang surface that is contactable to a placing surface,
    wherein the back-surface lower overhang surface is radially positioned outside an outer edge of the bottom wall, and
    wherein the back-surface finger receiving portion is the most radially outward portion of the container.

3. The application container according to claim 1, wherein the base portion includes a pair of side-surface finger receiving portions that are formed on opposite sides of the base portion in a direction orthogonal to a direction joining the side on which the mouth section is opened and a side opposite thereto, each of the side-surface finger receiving portions having a shape projecting outward or dented inward radially of the base portion.

4. The application container according to claim 3, wherein the pair of the side-surface finger receiving portions have respective shapes projecting outward radially of the base portion and
the pair of the side-surface finger receiving portions have respective side-surface lower overhang surfaces that are contactable to a placing surface outside an outer edge of the bottom wall radially of the base portion.

5. An application tool comprising:
the application container according to claim 1; and
an application section configured to be connected to the mouth section of the application container and being capable of applying a medicinal solution in the application container.

* * * * *